(12) United States Patent
Choi

(10) Patent No.: US 7,508,914 B2
(45) Date of Patent: Mar. 24, 2009

(54) RADIOLOGY DEVICE

(75) Inventor: Peter Choi, Orsay (FR)

(73) Assignee: Nano UV, Villebon Sur Yvette (FR)

( * ) Notice: Subject to any disclaimer, the term of this patent is extended or adjusted under 35 U.S.C. 154(b) by 0 days.

(21) Appl. No.: 11/404,773

(22) Filed: Apr. 17, 2006

(65) Prior Publication Data

US 2006/0193431 A1   Aug. 31, 2006

Related U.S. Application Data

(63) Continuation of application No. 11/024,962, filed on Dec. 30, 2004, now abandoned, which is a continuation-in-part of application No. 10/070,903, filed as application No. PCT/FR00/02524 on Sep. 13, 2000, now abandoned.

(30) Foreign Application Priority Data

Sep. 14, 1999   (FR) ................................. 99 11469

(51) Int. Cl.
   *H05G 1/64* (2006.01)
(52) U.S. Cl. ................... 378/98.12; 378/98.8
(58) Field of Classification Search .......... 378/62, 378/98.8, 98.2, 98.9, 210
   See application file for complete search history.

(56) References Cited

U.S. PATENT DOCUMENTS

| | | | |
|---|---|---|---|
| 3,912,936 A | 10/1975 | Cunninghame et al. | |
| 4,355,331 A | 10/1982 | Georges et al. | |
| 4,379,967 A | 4/1983 | McIntyre | |
| 4,467,351 A | 8/1984 | Wang | |
| 4,562,464 A * | 12/1985 | Kurihara ................... | 378/98.5 |
| 4,896,344 A | 1/1990 | Grady et al. | |
| 5,117,446 A | 5/1992 | Haaker et al. | |
| 5,138,642 A * | 8/1992 | McCroskey et al. ........... | 378/19 |
| 5,235,191 A | 8/1993 | Miller | |
| 5,308,986 A | 5/1994 | Walker | |
| 5,394,455 A | 2/1995 | Roeck et al. | |
| 5,452,337 A | 9/1995 | Endo et al. | |

(Continued)

FOREIGN PATENT DOCUMENTS

EP   0 644 712 A1   3/1995

(Continued)

OTHER PUBLICATIONS

Preliminary Search Report in corresponding French Application No. FR 991 146 9, 2000.

*Primary Examiner*—Hoon Song
(74) *Attorney, Agent, or Firm*—Finnegan, Henderson, Farabow, Garrett & Dunner LLP

(57) ABSTRACT

A radiology device includes an X-ray source for exposing a subject to the radiation of said source, a converter for converting the X-rays into optical images so as to form primary optical images, a transformer for transforming the primary optical images into secondary optical images, and a display for displaying the secondary images to a user. The transformer includes an optical chain including, in succession, from the output of the converter to the output of the device, an image enlargement assembly exposed directly to the primary images from the converter, an assembly for optical intensification of the enlarged images, and a photosensitive matrix sensor for making the secondary images.

23 Claims, 9 Drawing Sheets

U.S. PATENT DOCUMENTS

| | | | |
|---|---|---|---|
| 5,463,668 A | 10/1995 | Kagaya | |
| 5,778,044 A * | 7/1998 | Bruijns | 378/98.7 |
| 5,932,880 A | 8/1999 | Koguchi et al. | |
| 5,949,811 A | 9/1999 | Baba et al. | |
| 5,959,811 A | 9/1999 | Richardson | |
| 6,044,127 A * | 3/2000 | Van Bree et al. | 378/98.7 |
| 6,091,796 A | 7/2000 | Trissel et al. | |
| 6,130,932 A * | 10/2000 | Diepstraten | 378/98.7 |
| 6,198,801 B1 * | 3/2001 | Dillen | 378/98.7 |
| 6,226,351 B1 * | 5/2001 | Snoeren et al. | 378/98.12 |

FOREIGN PATENT DOCUMENTS

| | | |
|---|---|---|
| EP | 0 858 772 A1 | 8/1998 |

* cited by examiner

RADIOLOGY DEVICE

CROSS-REFERENCE TO RELATED APPLICATIONS

This is a continuation of application Ser. No. 11/024,962, filed Dec. 30, 2004 now abandoned, which is a continuation-in-part of U.S. application Ser. No. 10/070,903 filed Jul. 24, 2004 now abandoned, which claims priority of PCT Application Number PCT/FR00/02524, filed Sep. 13, 2000, and French Patent Application Number 9911469, filed Sep. 14, 1999, all of which are incorporated herein by reference.

BACKGROUND OF THE INVENTION

The present invention relates in a general manner to radiology devices. More precisely, the invention relates to a device making it possible to obtain high-resolution digital images of e.g. objects, organs or tissues which one wishes to examine (which for the sake of simplicity will be referred to subsequently in this text by the generic term "subject"), as well as of any desired region of the subject.

The subject can be e.g. a living body. It can also be material for which detection and/or characterization is sought (this can be the case for application of the invention such as the detection of explosives in a vehicle, a container, . . . ).

Radiology devices which implement an X-ray source and a module making it possible to visualize the track of the X-rays having passed through the subject have been known and employed widely for many years. The following overall typology can be established for these devices:

radiography devices, in which the subject is interposed between an X-ray source and an X-ray sensitive film. This type of device which was historically the first to be used and which is the most widespread, thus provides static images of the subject which must remain immobile during exposure thereof to the X-rays for a time sufficient to obtain an impression of the film by the X-rays. This type of device has rendered great service; it nevertheless has drawbacks, the main ones of which are the following:

limitation to the production of static images, thus precluding visualization of the dynamic evolution of the subject in order to characterize certain aspects of its functioning, repeated exposure of radiologists to X-rays and health risk stemming therefrom, fluoroscopy devices on the other hand offer access to dynamic images. In these devices, the subject is interposed between an X-ray source and visualization means which in real time convert the X-radiation into a visible image. These means may thus offer:

direct visualization. In this case, the radiologist directly visualizes the "primary" images which are the first images formed by the visualization means from the X-rays. The visualization means then consist of a converter of the phosphor coating screen type.

or indirect visualization. In this case, the device comprises means for acquiring the primary images at the output of a converter (the latter possibly being of the phosphor screen type), via a chain which may include a video camera filming the entire field of an output screen of the converter so as to form a "secondary" image, means for digitizing the image and means for processing, storing and distributing the images to various terminals (which may be on different sites).

In both cases (direct and indirect visualization), the visualization means allow dynamic viewing of the temporal evolution of the subject (visualization of the functioning of moving organs), thereby constituting an advantage and offering enhanced possibilities of implementation (recording of sequences illustrating the functioning of the subject, live operative assistance, etc.).

For medical applications, these fluoroscopy devices also have drawbacks however, among them being inferior image quality to that of radiography images (especially in terms of contrast), because of the necessary reduction in the intensity of X-ray emission for reasons of safety of the radiologist (and of the patients), the exposure to the radiation being lengthy.

To attempt to diminish the importance of this problem related to fluoroscopy devices, manufacturers have implemented intensifiers which make it possible to convert the X-radiation into an optical image with high efficiency (that is to say by producing a high number of photons per incident X-ray).

By increasing the intensity of the images produced and by thus improving their contrast and their sharpness, these devices make it possible to lower the intensity of the X-radiation to a level below that implemented in radioscopy; they can function in direct or indirect visualization mode. In both cases, the intensifiers comprise an output interface for displaying the primary images to an observer, or transmitting them to an image acquisition chain.

The fluoroscopy devices thus constitute an advantageous means of carrying out good-quality radiological examinations. It is moreover possible to carry out the examination of the subject according to two types of procedures:

based solely on images covering a single field containing the zone(s) of interest, or else by taking successive snapshots of different zones of interest.

The second type of procedure offers the advantage of greater flexibility of use, making it possible initially to take a wide-field snapshot so as to identify zones of interest, then to center the device successively on each of these zones.

For this type of use, especially in indirect fluoroscopy, image acquisition and enlargement means are generally provided for gathering the primary images as a whole, and then carrying out an enlargement of a part of the primary image centered on the desired zone.

However, this last type of use has the drawback of degrading the resolution of the secondary images which will be visualized, given that the secondary images which are enlarged have previously been discretized by the acquisition means: the resolution of the image observed is in this case N times lower than the resolution of the acquisition means, N being the enlargement coefficient.

Moreover, in the case of intensifier devices, the resolution of the primary image is already greatly limited by the resolution of the intensifier itself, which is commonly of the order of from 1 to 2 pairs of lines per millimeter only.

Such a drawback can result in the impossibility of detecting certain details of very small size, such as for example certain early symptoms of cancer of the stomach which are of millimeter size.

Furthermore, the intensifiers of fluoroscopy devices generally comprise curved input screens which produce aberrations in certain parts of the image.

BRIEF SUMMARY OF THE INVENTION

An aim of the invention is to alleviate the drawbacks mentioned hereinabove and to make it possible, on the one hand to construct a radiology device providing high-resolution images of any desired part of a subject, and on the other hand to implement such a device according to an advantageous process.

Another aim of the invention is to make it possible to construct a real-time radiology device in which inter alia the images are almost undeformed.

Another aim of the invention is to efficiently provide access to an increased sensitivity range over which the signal can be detected.

Another aim of the invention is to reduce as much as possible the noise associated with the images obtained.

Another aim of the invention is to provide efficient, simple and reliable means for obtaining images with different energy levels from the same subject. And according to a specific aspect, another aim of the invention is to provide efficient means for increasing the contrast associated to such images.

In order to achieve these aims, the invention proposes, according to a first aspect, a radiology device comprising an X-ray source for exposing a subject to the radiation of said source, means for converting the X-rays into optical images so as to form primary optical images, means for transforming the primary optical images into secondary optical images, means for digitizing the secondary images and means for displaying the secondary images to a user, characterized in that the means for forming the secondary optical images comprise an optical chain comprising in succession, from the output of the converter to the output of the device, an image enlargement assembly exposed directly to the primary images from said conversion means, an assembly for optical intensification of the enlarged images and a photosensitive matrix sensor for making said secondary images.

Preferred, but nonlimiting aspects of the device according to the invention are the following:
- the enlargement assembly is a variable enlargement assembly, able to enlarge the images according to a desired enlargement coefficient within a given range.
- the enlargement assembly is made up solely of optical elements performing no discretization of the images.
- the device comprises means for moving the elements of the optical chain in a plane generally parallel to the midplane of the conversion means.
- the device comprises a central control unit for controlling the movement of the elements of the optical chain.
- the central control unit is physically distanced from the other elements of the device.
- the device comprises means of monitoring the exposure and the degree of enlargement of the images.
- the assembly for optical intensification of the images comprises components of the MCP type.
- the device comprises means for digitizing the secondary images arising from the photosensitive matrix sensor.
- the device comprises interfaces for distributing the images destined for digital peripherals.
- the device comprises a screen for visualizing the digitized secondary images.
- the means for converting the X-rays into optical images consist of a fluoroscopy screen of the phosphor coating screen type.
- said optical chain is directed along a different axis from the normal to the midplane of the means for converting the X-rays into optical images, the device comprises a mirror for deflecting the primary images to the optical chain and the device comprises a shield for protecting the elements of the optical chain from the X-rays.
- the optical chain comprises a refocusing lens.
- the device comprises a mirror for separating the images arising from the intensification assembly and a digital video camera.
- the optical coupling between the intensification assembly and the sensor is effected by optical fibers.

According to a second aspect, the invention also pertains to the use of the device described hereinabove, for real-time radiological examinations (especially for applications in the industrial and maritime sectors).

BRIEF DESCRIPTION OF THE SEVERAL VIEWS OF THE DRAWINGS

Other characteristics, aims and advantages of the invention will become more clearly apparent on reading the following description of three embodiments of the invention, given with reference to the appended drawings, in which.

DETAILED DESCRIPTION OF THE INVENTION

Figure 1:
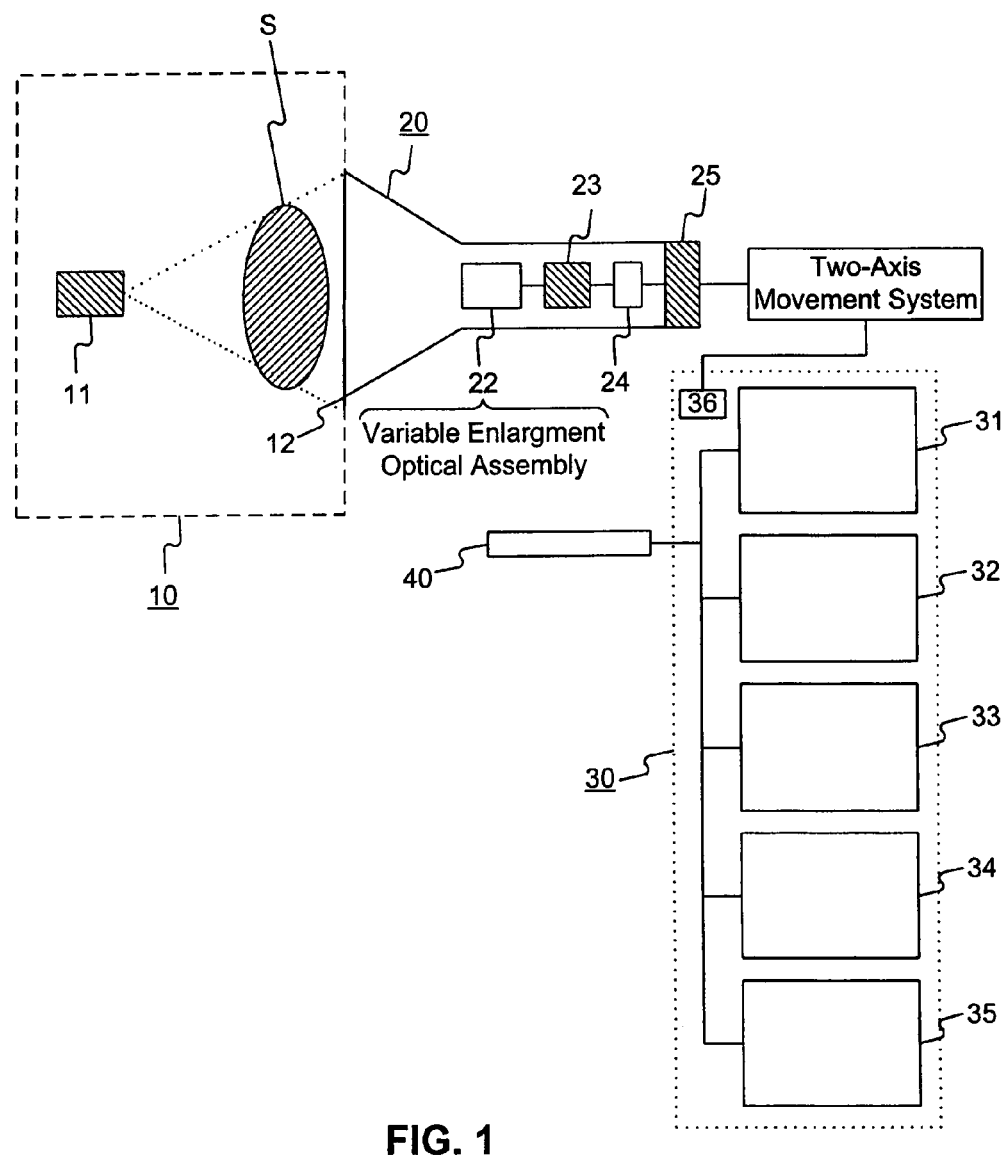
FIGS. 1 to 3 are representations of the block diagram type of three embodiments of a radiology device according to the invention.

With reference firstly to FIG. 1, there has been schematically represented a first module 10 comprising an X-ray source 11, and a fluorescent screen 12. This module 10 can be a conventional fluoroscopy module, the screen 12 delivering as output from the module 10 a primary visible image corresponding to the track of the X-rays emitted by the source 11 after they have passed through a subject S interposed between the source 11 and the screen 12.

The device also comprises a second module, referenced 20, for acquiring the primary images and for forming secondary images. As will be seen in greater detail subsequently in this text, the spatial coverage of these secondary images can correspond to that of the primary images formed on the fluorescent screen 12, or else to only a part of these primary images.

The module 20 comprises in a lightproof enclosure:
- an optical assembly 22 for variable enlargement of images, which is focused on the fluorescent screen 12,
- an image intensifier assembly 23 for producing, from the images enlarged by the assembly 22, images of greater luminous intensity,
- a refocusing lens 24 for reforming intensified images at the output of the assembly 23,
- an optical sensor 25, on which the lens 24 is focused, for gathering the enlarged and intensified image and for converting it into a discretized analog secondary image. This sensor can be a CCD type matrix for example.

The optical elements 22, 23, 24 and 25 of the module 20, which are assembled in series and thus form an optical chain, are furthermore mounted on a two-axis movement system which is represented in the figures. This system can move these optical elements in the two directions coplanar to the fluorescent screen 12 so as to bring in particular the enlargement assembly 22 opposite any desired zone of this screen.

The device comprises a third module 30 for processing and distributing the images arising from the module 20. This module 30, which constitutes a central control unit for the device, comprises in the embodiment represented in FIG. 1 the following elements which are interlinked:
- a unit 31 comprising electronic means for digitizing analog signals delivered by the sensor 25, and for processing these signals,
- a unit 32 for the local storage of digital images,
- an interface unit 33 for communicating video signals (originating from the sensor 25 and/or destined for external video peripherals),
- an interface unit 34 for communicating digital signals,
- and an exposure and enlargement control unit 36.

The module 30 also comprises means 36 (represented in the figure) for controlling the system for moving the elements of the optical chain of the module 20, in particular of the enlargement assembly 22.

The device finally comprises an interface 40 for local visualization of images which can consist of a high-resolution video screen hooked up to the units of the module 30. This interface 40 can be a digital screen receiving the secondary images digitized by the unit 31 of the module 30.

This device can function according to a continuous mode, likewise the subject of the invention, described hereinbelow:

The subject having been exposed to the radiations of the source 11 so as to form a dynamic image on the screen 12, the radiologist can visualize in real time on the screen 40 a secondary image corresponding to the entire primary image formed on the screen 12, covering for example a widened field of the subject inside which the radiologist is searching for specific zones of study.

By virtue of the means of control of the movement system of the module 30 and by virtue of the exposure and enlargement control unit 35, the radiologist can then control the continuous movement of the optical chain formed by the elements 22, 23, 24 and 25 in a plane parallel to the plane of the screen 12, as well as the degree of enlargement of the image formed at the output of the lens 22 and transmitted to the other optical elements of the chain. This degree of enlargement can be fixed by the radiologist at any desired value within a given range, which depends on the choice of the assembly 22.

It will be noted that all or some of the elements of the module 30 may be situated some distance from the other constituents of the device (in particular from the modules 10 and 20), for example in a separate room dedicated to the control of the device and to the visualization of the images, or even in a separate building. In this case, the length of the link between the module 30 and the module 20 (which consists of at least one cable for transmitting the images from the optical sensor 25 to the module 30, and for transmitting the commands arising from the module 30 to the elements of the optical chain of the module 20) is suitably adapted.

To control these movement, exposure and enlargement means, the radiologist is provided with an interface (not represented) which can be associated with the visualization screen 40. This interface can use a control cable, linked to the module 30 to manually activate the image selection and capture process.

The screen 40 can be of any known type, inter alia a liquid crystal screen. The module 30 can also be associated with a PC type control computer supplemented with the commands of the device (commands for exposure, for moving the optical chain and for enlargement, etc.). Such a PC can contain a program for using the device, implementing a menu for the control of the device which is displayed on the screen 40 in combination with the output images from the device.

It is important to note here that according to the invention the resolution of the image is in no way altered by modifying the degree of enlargement, given that the assembly 22 which is composed solely of optical elements does not carry out any discretization of the image.

On the basis of images having a widened field, it is thus possible for the radiologist to identify zones of specific interest, then to move the optical elements and to zoom in on the chosen zone(s), while obtaining at the output of the assembly 22 an image whose resolution is in no way altered.

It will be noted that according to the invention, the chaining together of the snapshots of various zones with various degrees of enlargement is carried out in a continuous manner, this being an advantage in terms of ease of use.

The image (enlarged or otherwise) is transmitted by the assembly 22 to the optical intensifier 23, which will preferably be made up of so-called channel multiplier plate (or MCP according to the acronym in use) elements. An exemplary embodiment of such an element will be found in U.S. Pat. No. 3,660,668. It is also possible to link several intensifier elements of the MCP type in series, and thus to obtain an optical gain of the order of $10^3$ to $10^7$.

By virtue of the MCP optical intensifier 23 which can be operated in series, the intensity of the radiation of the X-ray source 11 can be limited to a level lower than that conventionally implemented in intensifier fluoroscopy devices.

It will be noted furthermore that an optical intensifier constructed from elements of the MCP type does not include elements of domed geometry such as the input screen of x-ray image intensifiers which is conventionally employed in fluoroscopy devices.

This constitutes an advantage insofar as this characteristic does not introduce any distortion of the image. The enlargement assembly 22 is thus the only optical element of the device comprising curved parts, so that the optical aberrations and deformations of certain zones of the image are reduced to the minimum.

The radiologist can thus carry out a continuous examination of various zones of the subject, by moving the optical chain formed by the elements 22, 23, 24 and 25 and by controlling via the unit 35 the enlargement of the image on each desired zone in succession, the enlargement of the image not altering the spatial resolution of the image.

It will be noted that the enlargement of the image is furthermore continuously adjustable by way of the control unit 35, thereby further increasing the flexibility of use of the device according to the invention.

A unit for programming successive movements and enlargements can also be integrated into the module 30 in order to undertake a program of predetermined examinations.

The assembly 22 can also be physically detached from the other elements 23, 24, 25 of the optical chain of the module 20, and it is also possible to control only the moving of this assembly 22 opposite the fluorescent screen 12, image transmission means such as an optical fiber link then being provided between the assembly 22 and the intensifier 23.

It should also be noted that the radiological examination process described hereinabove can be conducted without changing the intensity of the X-radiation to which the subject is exposed. Indeed, since the enlarging of the image does not alter its resolution, it is not necessary to increase the dose of radiation in order to visualize a zone of detail of restricted dimension.

The digital images can be stored by the unit 32 and distributed to any type of digital peripheral (or analog peripheral by virtue of the video signals communication interface unit 33). These peripherals may be visualization screens, high-resolution printers, remote means of storage and archiving, etc. They may be located on the same site as the device described above, or be situated remotely on other sites furnished with a link with the module 30.

By virtue of the device described hereinabove, the radiologist can also take a first fast snapshot of a widened field containing the entire subject, then study the image produced at his/her leisure, the source 11 being inactivated. After having identified the specific zones which he/she wishes to study in greater detail, the radiologist can then reactivate the source 11 to obtain detailed images of these zones with the full resolution of the assembly of sensors 25. This mode of use of the invention makes it possible to further reduce the level of exposure of the radiologist and of the subject to radiation.

The module 30 can also comprise, in particular in the unit 31, all the known means for digitally processing the image, such as means for manipulating the image (choosing zones, rotation, processing of contrast and thresholding operations, etc.).

It will be noted that the resolution of the images produced by the device according to the invention is very markedly greater than that of the images produced by the fluoroscopy device implementing image intensifiers. The resolution of the images of these devices is in fact limited by the resolution of the intensifiers, which is at best of the order of from 1 to 2 pairs of lines per millimeter; the use of intensifiers of the MCP type, combined with the absence of discretization of the images during their enlargement, makes it possible to achieve a greater resolution.

It will furthermore be noted that by virtue of the means of processing and of distribution of the digital image of the module 30, the device according to the invention offers multiple possibilities of practical utilization. The files of the images may in fact be easily transmitted by electronic means to other sites so as, for example, to solicit the opinions of different experts.

It will also be noted that the use of printers, or of any other type of known peripheral for registering and/or printing on a medium such as paper (conventional or of photographic quality depending on requirements) the digital images arising from the module 30, constitutes an extremely flexible and economical means of obtaining negatives equivalent to radiographic negatives, so that the device according to the invention can be used as a radiography or fluoroscopy apparatus.

Figure 2:
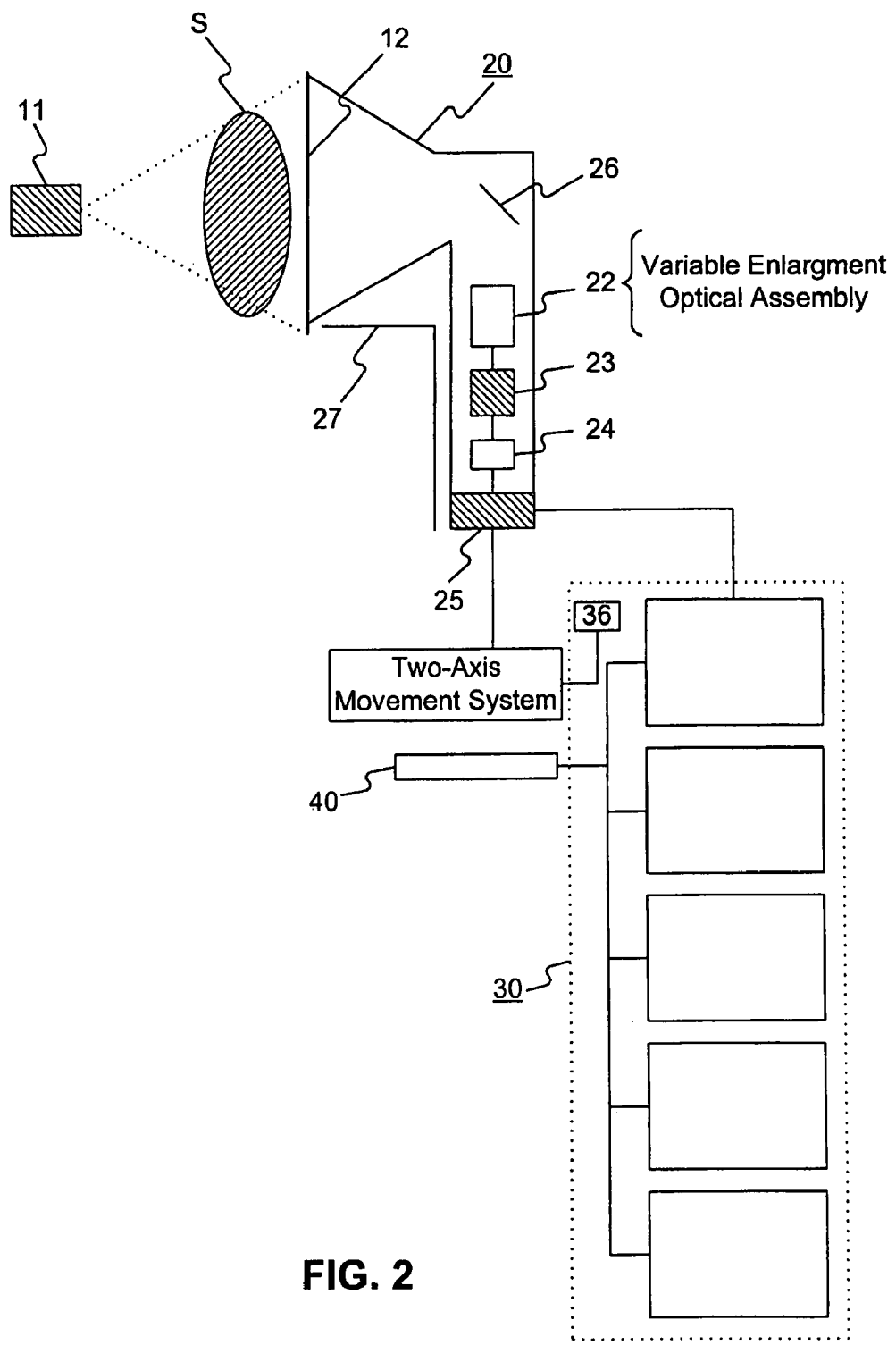

FIG. 2 represents a second embodiment of the device according to the invention in which the module 20 is folded at 90°, the image from the fluorescent screen 12 being deflected to the optical chain of the lens 22 by way of a deflecting mirror 26.

In this embodiment, the optical chain of the module 20 is oriented generally parallel to the plane of the screen 12, a 90° deflecting mirror 26 deflecting the images from the screen 12 to the enlargement assembly 22. A "T"-shaped shield 27 is also provided in order to protect the elements of the optical chain from the X-radiation.

Figure 3:
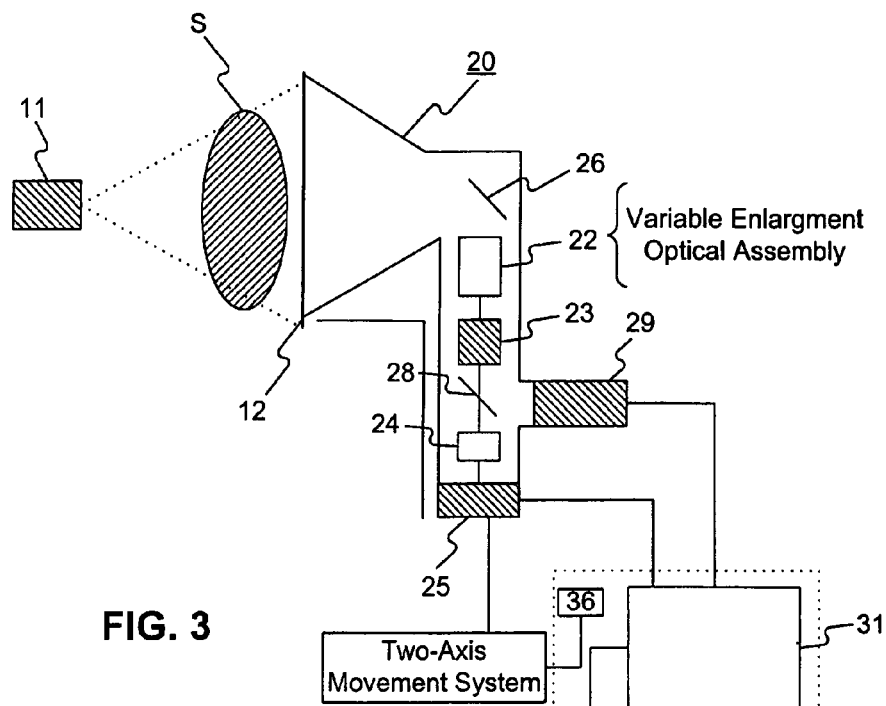

FIG. 3 presents a third embodiment of the invention in which between the image intensifier and the refocusing lens 24 there has furthermore been interposed a prismatic mirror 28 for separating the image, so as to separate the images transmitted by the optical intensifier into two beams directed respectively towards the sensor 25 and towards a digital video camera 29, these two elements being linked to the unit 31 of the module 30.

This third embodiment allows separate acquisition of dynamic images (by the camera 29) and of static images (by the sensor 25); this arrangement makes it possible to further increase the flexibility and the performance of the device.

Figure 4:
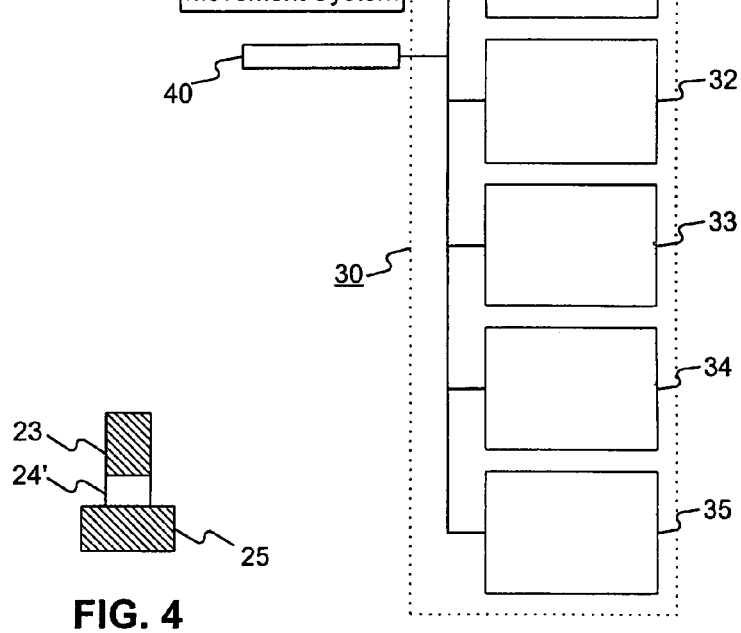
FIG. 4 is a schematic representation of image acquisition elements which can be implemented in a radiology device according to the invention.

FIG. 4 represents a variant embodiment of elements of the optical chain of the device according to the invention, in which the image intensifier 23 is linked to the sensor 25 by a network of optical fibers 24' in replacement for the refocusing lens 24.

Of course, the device according to the invention is not limited to the embodiments described hereinabove, but may be embodied according to any variant within the scope of the person skilled in the art.

The use of such a device is not limited to the medical sector; the device described hereinabove can in fact also be implemented in any other sector of application of radiography apparatuses, and of X-ray examination in general.

In particular, the use of such a device for the inspection or nondestructive qualitative analysis of materials, for example in the industrial sector (inspection of walls or of pipelines, etc.), maritime sector (inspection of ships or of submarines, etc.), etc., makes it possible to access the advantages of real-time flexibility of use described hereinabove with regard to medical examination.

Specific embodiment which comprise a radiology device as mentioned above, and which corresponds to advantageous methods for using such a device, shall now be described.

These embodiments generally use a x-ray source which delivers x-rays in a pulsed manner.

More precisely, the pulses of this x-ray source are ultra-short pulses, with a duration which is typically less than 100 nanoseconds.

Figure 5:
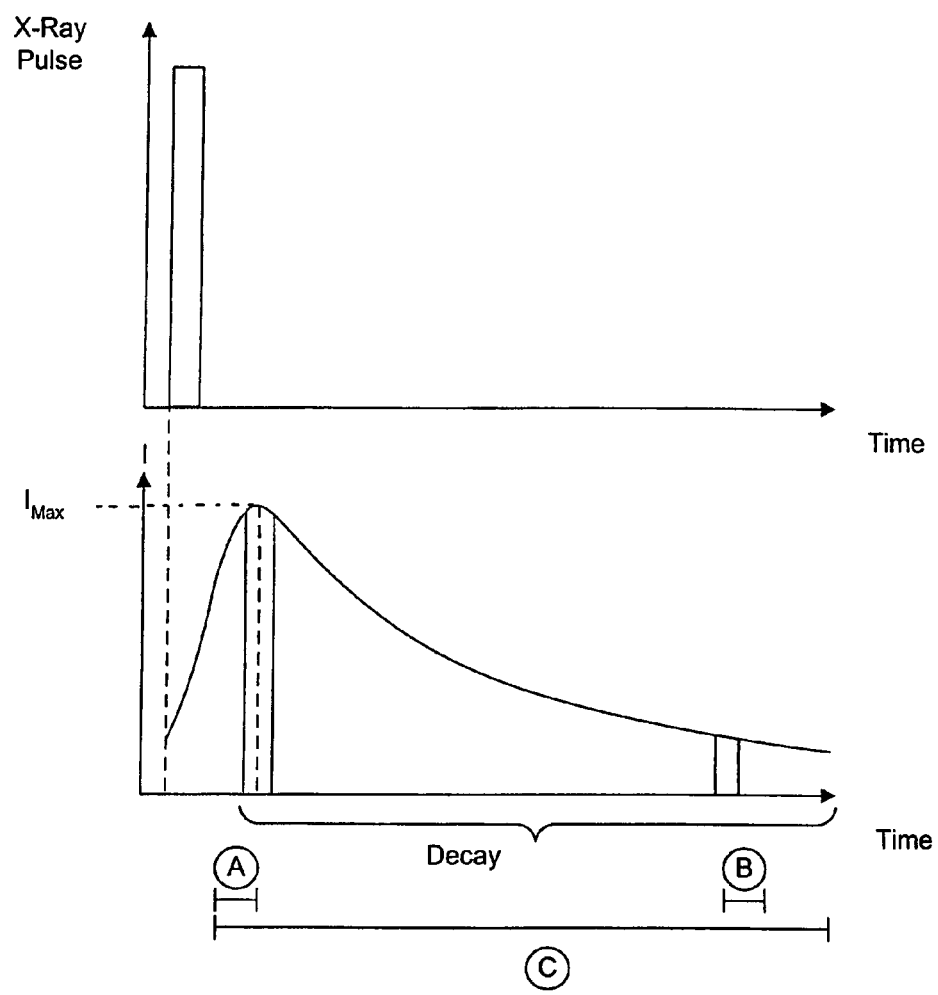
FIG. 5 is a graph representing the evolution with time:
in its upper part, of a short pulse from a pulsed x-ray source for supplying x-rays to a device according to the invention,
in its lower part, of the corresponding signal observed on the means for converting the x-rays into optical images.

FIG. 5 schematically illustrates such an ultra-short pulse (upper part of the figure), and the resulting intensity I of the primary visible image generated by the converting means (i.e. means 12 mentioned above, such as a fluorescent screen).

Both upper and lower curves of this figure indicate time as their horizontal axis.

The intensity I rapidly raises up to a maximum intensity Imax, and then progressively decreases along a decay curve.

Thus, after the x-ray pulse of the source has been terminated, a primary visible image still remains within the decay time.

The lower part of FIG. 5 illustrates several time windows A, B and C.

Time window A corresponds to a time interval defined around the maximum intensity Imax, and having a very reduced width (e.g. in the order of 10 to 100 nanoseconds).

Time window B corresponds to another narrow window, located in the end part of the decay.

Time window C covers essentially the whole duration of the decay (i.e. typically between a microsecond and a second).

These three time windows illustrate three possibilities for gating a module 20' which is identical or similar to the module 20 mentioned above.

More precisely, the module 20' comprises in particular an image intensifier assembly (i.e. 23) and an optical sensor 25 (typically a CCD type matrix). As a possible difference with module 20 described above, even though it is very advantageous that the module 20' comprises an optical assembly 22 for variable enlargement such assembly 22 can be omitted in some embodiments.

The "gating" of module 20' corresponds to a gating of its image intensifier, and/or a gating of its optical sensor.

By "gating" an element (image intensifier, and/or optical sensor), is meant the selective and temporary application of power to the "gated" element.

And the time windows A, B and C illustrate three options for gating the module 20'—i.e. three options for defining a time of beginning and a time of end of the application of power to the gated element(s).

In all cases, the gating is synchronized with the pulses from the x-ray source, by synchronizing means connected to the x-ray source and to the gated element(s) of module 20'.

It can be appreciated that these different time windows correspond to different values of the intensity I.

Each option for gating the module 20' defines a specific conversion factor of the converting means 12.

The intensity of the visible signal observed on the optical sensor 12 can thus be expressed as the product of the following parameters:

Intensity of the x-rays which illuminate through the subject—this parameter is determined by the x-ray source, Transmission factor of the subject—this parameter is determined by the subject, Gain from the image intensifier (generally noted G)—this parameter G is determined by the image intensifier, General conversion factor for the converting means 12—this parameter is determined by the converting means 12, Gate conversion factor (generally noted K) for the gate selected for module 20'—this parameter K is determined by the gate (i.e. time window in decay) selected.

It is furthermore specified that a given module 20' defines a range over which the visible primary images formed by the conversion means 12 can be detected and exploited.

The two extreme values of this range are defined respectively by the minimum intensity of visible light which can be detected, and the maximum intensity of the same light.

We will come back to this notion of range and show how the invention allows to stretch the range of a given type of module.

Furthermore, in the example of FIG. 5, the time window B corresponds to a gate conversion factor which is significantly lower than the gate conversion factor associated with time window A.

For a given device (i.e. for a given x-ray source, image intensifier and converting means) and for a given subject, the value of the gate conversion factor thus determines the value of the intensity of the visible image generated by the optical sensor 25.

Figure 6:
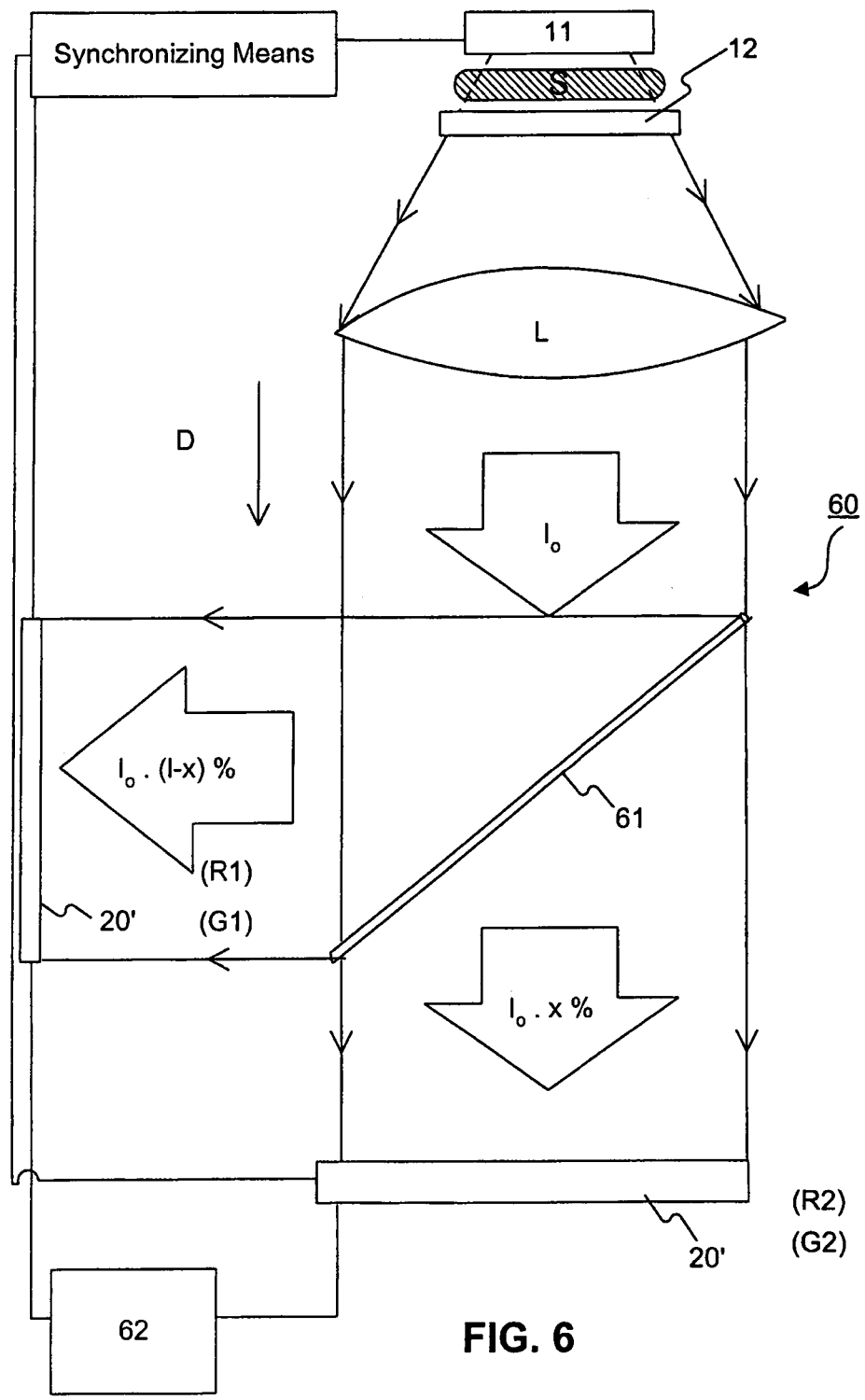
FIG. 6 is a schematic representation of an arrangement corresponding to a particular embodiment of the invention, where at least two photosensitive sensors are used.

FIG. 6 shows an arrangement 60 which corresponds to a specific embodiment of the invention which exploits a specific gating.

Figure 7:
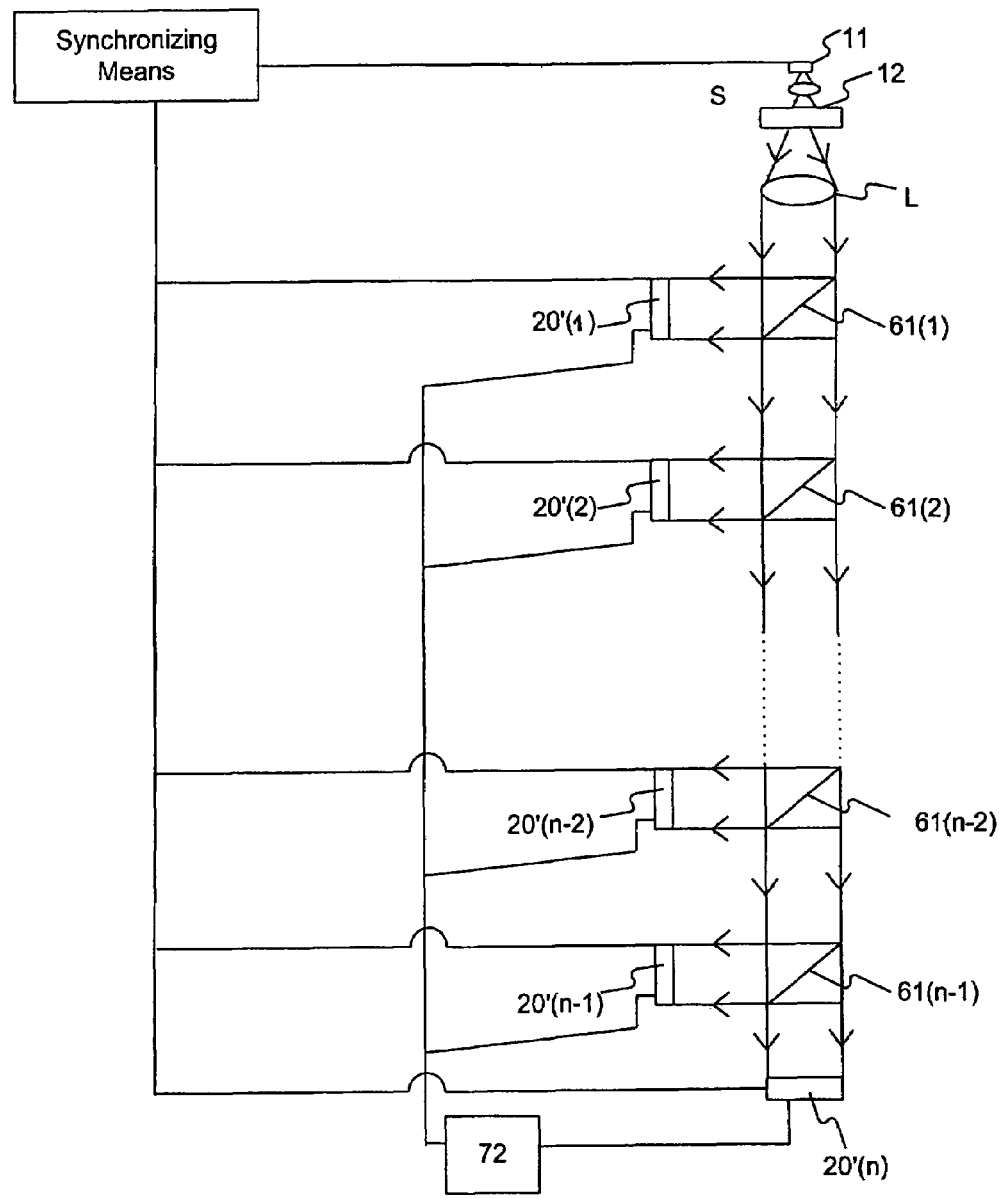
FIG. 7 is a schematic representation of an arrangement corresponding to the embodiment of FIG. 6, comprising more than two photosensitive sensors.

This arrangement 60 comprises at least two modules 20' (on FIG. 6 only two such modules are represented but the arrangement could comprise any number of modules 20' as will be illustrated in FIG. 7).

The arrangement 60 also comprises converting means 12 such as mentioned above, and a lens L for collimating the "primary" visible light of the primary image formed by these converting means along a single direction D.

This primary visible light has an intensity $I_0$ (expressed either as a global or mean intensity, or as an elementary intensity of a particular area of the converting means 12).

The arrangement 60 also comprises a beam splitter 61 which is adapted to transmit (i.e. let pass without alteration) a given ratio of the incident intensity $I_0$ (this ratio being of x %-x can have any value between 0 and 100).

Thus, a transmitted beam with an intensity $I_0*x$ % passes through the splitter 61, and the rest of the intensity ($I_0*(1-x)$ %) is reflected by said splitter.

The reflected beam is directed onto a first module 20', and the transmitted beam is directed onto a second module 20'.

Each of the modules 20' is individually gated, each gating being defined by the product of:

The gain G from the image intensifier, and

The gate conversion factor K associated with the particular gate selected.

The gating of each module is made along a very narrow time window (i.e. 10 to 100 nanoseconds—however these values are not limitative), so that a single gate conversion factor can easily be defined for each gating (in any event, even for a wider gate it is always possible to define a law for obtaining a single value of the gate conversion factor—i.e. by a mean value or another law).

In reference to FIG. 6 where two modules 20' are represented, a first module (say the one which receives the reflected beam) is gated with a gain G1 and with a gate conversion factor K1, and the other module (the one which receives the transmitted beam) is gated with a gain G2 and with a gate conversion factor K2.

Each module is associated with a module range R of intensities, expressed as the ratio between the maximum intensity which can be detected and the minimum intensity which can be detected.

An example of a range value is e.g. (1000:1): in such case the maximum intensity detectable is 1000 times higher than the minimum intensity detectable.

The ranges for all modules can be either all different, or all the same, or some ranges can be different and some can be the same (the latter being possible in the case where there is more than two modules).

In the case of the modules of FIG. 6, the first module has a range R1 and the second module a range R2.

In such case, the first module shall produce a secondary image over an intensity range defined by $R1*(I_0*(1-x)$ %).

And the second module shall produce a secondary image over an intensity range defined by $R2*(I_0*x$ %).

It shall thus be understood that the combination of the two modules covers a range which can be significantly wider than the standard range of a module.

More precisely, the arrangement 60 comprises means 62 for retrieving the secondary images formed by the modules 20' and for combining them on a time-coherent basis.

"Combining on a time-coherent basis" means that the secondary images from the different modules—two or more—are combined in a synchronized manner, with no time lag between the images. This combination is typically performed in real time.

The "combination" can be a division of the intensity of a first secondary image by the intensity of a second secondary image—both intensities being assessed at the same moment.

As an example, if one assumes that:
R1=R2=(1000:1),
G1=G2=100,
K1=10 and K2=1,
and x=1, the output of the first module 20' of FIG. 6 shall have an intensity of about $990*I_0$ (i.e. $G1*K1*0.99*I_0$) with a range of 1000:1, and the output of the second module 20' of FIG. 6 shall have an intensity of about $I_0$ (i.e. $G2*K2*0.01*I_0$) with a range of 1000:1.

In other words, the global range of the arrangement has a range of $9.9*10^5$—i.e. in the order of $10^6$.

The range between the minimum and maximum intensity detectable is thus stretched in a very significant manner.

It is to be noted that the existing systems can comprise means for stretching the range, by increasing the sensitivity of an image intensifier, dynamically.

But such known means necessitate costly and complex arrangements in the image intensifier—whereas the solution exposed above is simple in design and in operation.

On the contrary, the invention provides simple and efficient means for stretching the range of detection of images generated by a device as described in this text.

And it is to be noted that this stretch of the range can be adapted as desired, by selecting adapted values for R1, R2, G1, G2, K1, K2 and x.

FIG. 7 illustrates an embodiment based on the principle exposed in reference to FIG. 6, where an arrangement 70 comprises n modules—n being more than two. The modules are here referred as 20' (i), with i between 1 and n.

Each module 20' (i) (except the last module) is associated to a respective beam splitter 61(*i*), which lets a given proportion of intensity pass through and reflects the rest.

Each module 20' (i) can have different values of gain G1, factor Ki and range Ri—and the proportion xi of the beam splitter associated to each module can be different.

All these values of G1, Ki, Ri and xi can be selectively adapted as a function of the stretch desired for the global range of the arrangement.

Here again the arrangement comprises means (here 72) for retrieving the secondary images formed by the modules 20' and for combining them on a time-coherent basis.

The above arrangements can be used with a pulsed source as already exposed. However, it is also possible to use it with a classical continuous (DC) source since such specific arrangement shall in any event provide an advantage for stretching the range of light detected.

If the arrangement is used with a DC source, only the ranges and the values of the proportion transmitted through the beam splitter(s) define the global stretch. In other words, in such a configuration the parameter κ has a constant value, whereas the parameter G still has an influence on the global stretch.

However, using a pulsed x-ray source with such arrangement is particularly advantageous.

Indeed, in the case e.g. of applications such as the detection of very small objects in a tank filled with liquid (this can be the case e.g. in the domain of transportation of nuclear materials), said tank being itself in a larger container filled with air, an arrangement of the type described in reference to FIGS. 6 and 7, operated by a pulsed source, allows to use a "stronger" x-ray source (i.e. a source having a higher energy—as expressed in MeV, and/or a higher fluence (or flux since the fluence can be related to a flux)).

For such applications, where it is desired to detect a potential object in the water tank, x-rays with adequate penetrating power—i.e. having an energy which is typically in the MeV range—are generally used in the known devices.

At such x-ray energy, the mass absorption coefficient of water is generally close to the mass absorption coefficient of the object to be detected.

In order to discriminate the object to be detected from the surrounding water, in the case of these known devices, it is possible to increase the energy of the x-rays and/or their fluence.

However, increasing the energy of the x-rays would lead to a reduction in contrast of the objects visualized by the device, and increasing the fluence would lead to saturating the image obtained, since the air which surrounds the water tank would then produce a saturated image (since this surrounding air has an absorption power significantly lower than the absorption power of water).

By stretching the range (also called dynamic range, and corresponding to the range between the minimum visible brightness to the maximum visible brightness), the arrangement of the invention allows to discriminate the object to be detected from the surrounding water, by increasing the fluence of the x-ray source, without putting at risk the resulting image since it could saturate it.

With a pulsed x-ray source and an appropriate gating (not necessarily with the arrangement of FIGS. 6 and 7—but also with a device as exposed in reference to FIGS. 1 to 4), many drawbacks of the prior art are thus eliminated.

Figure 8:
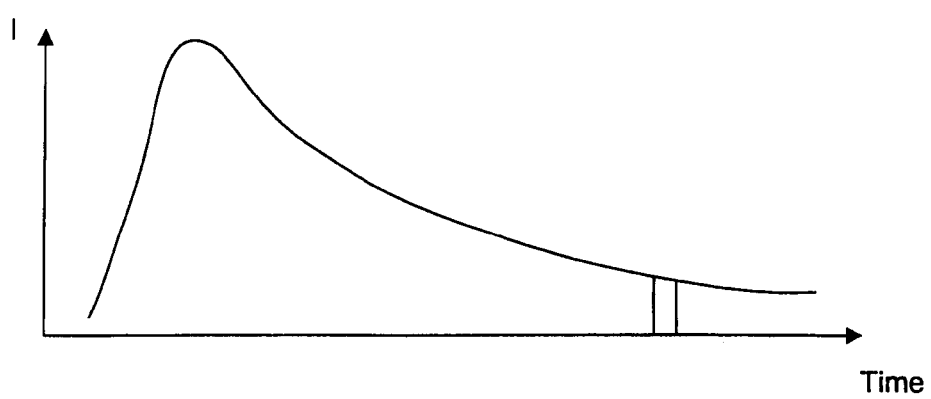
FIG. 8 is a graph illustrating the decay of a signal observed on the means for converting the x-rays into optical images, and a particular gating of such signal.

If the visible signal to be observed as an output of the arrangement is likely to be saturated, it is indeed possible to select a gating in the end part of the decay (as illustrated in FIG. 8).

It is e.g. possible to gate the module 20 (or 20') so that it detects between Imax/100 and Imax/1000.

Such "end of decay gating" allows to adapt the range for the downstream optical sensor (CCD or other), and a signal which would have been saturated at observation can now be exploited by a normal optical sensor.

Using a pulsed x-ray source furthermore allows a better real-time operation and more efficient detection on moving subjects.

Figure 9:
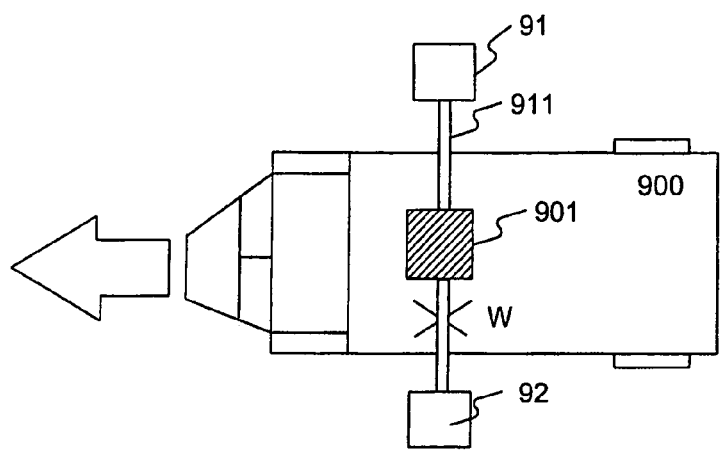
FIG. 9 is a schematic representation of a moving truck passing in front of an embodiment of a device according to the invention, for real-time detection of subjects within the truck in movement.

As an illustration, FIG. 9 shows a truck 900 which moves (along the direction of the arrow) and passes in front of a x-ray source 91 which generates an x-ray beam 911 having a width W, said beam being then directed onto an assembly 92 which comprises converting means 12 such as mentioned above and a module (20 or 20').

If the x-ray source was a DC source, for a given energy of the source (in Coulombs) and a truck moving at a given speed, the source should be powered with a resulting value of intensity (in mA) which is determined by the energy of the source, the width of the x-ray beam and the speed of the moving subject.

A DC source indeed continuously scans the moving subject whereas in the case of a pulsed x-ray source the images taken of the moving subject are ultra short "photographic" flashes which can flash moving subjects even at high speeds.

An application such as the "flash" of large subjects such as moving trucks should be carried out with a converting means (i.e. a large phosphor or fluorescent screen)—and it has been exposed in reference to FIGS. 1 to 4 that specific solutions were provided in this respect, for selectively analyzing some areas if desired.

Another aspect associated with a pulsed x-ray source and a gating of module 20 or 20' is the reduction of noise which can be obtained.

For that purpose, a specific type of gating can be carried out on the module.

Figure 10:
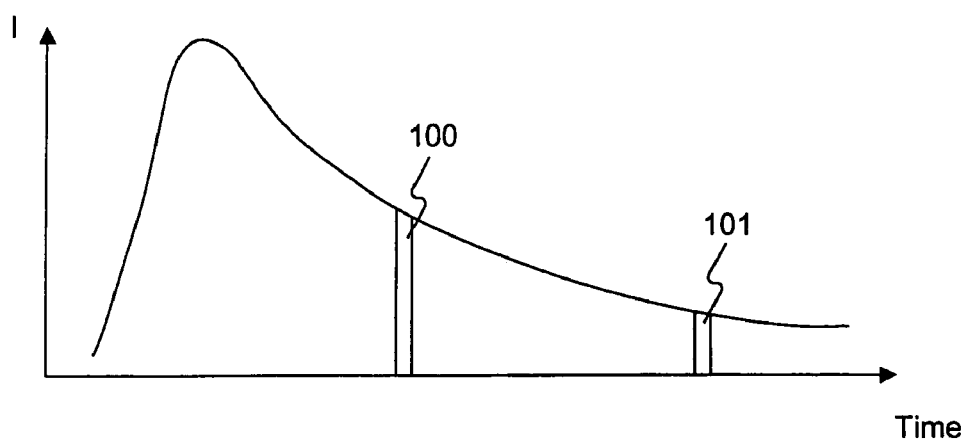
FIG. 10 is a graph illustrating the decay of a signal observed on the means for converting the x-rays into optical images, and another particular gating of such signal, adapted in particular to reduce the noise of the signal observed.

Such gating is a "multiple gating", as schematically illustrated in FIG. 10.

This figure shows the decay which follows a single pulse of the x-ray source, with two successive gates 100, 101.

The decay corresponds to the evolution in time of the same signal, which can indeed be gated at two (or more) successive times.

Each gating shall produce a signal.

For all gates, the information part of the signal on the optical sensor is the same, but the noise component will change.

By combining the signals of all (two or more) gates, e.g. by arithmetic averaging, it is thus possible to reduce the noise component of the signal (i.e. the noise introduced by the MCP image intensifier)—and thus to retrieve the information part of this signal. More complex mathematical treatments can be used for combining the signals in order to reduce the noise component.

It should be noted that this retrieving of the information part of the signal uses the fact that the information part is the same for all gates, since the pulse of the x-ray source is ultra-short and the duration of the decay is also very short.

It is specified that a significant part of the noise comes from the MCP image intensifier, which is triggered in synchronization with the pulses of the x-ray source.

Figure 11:
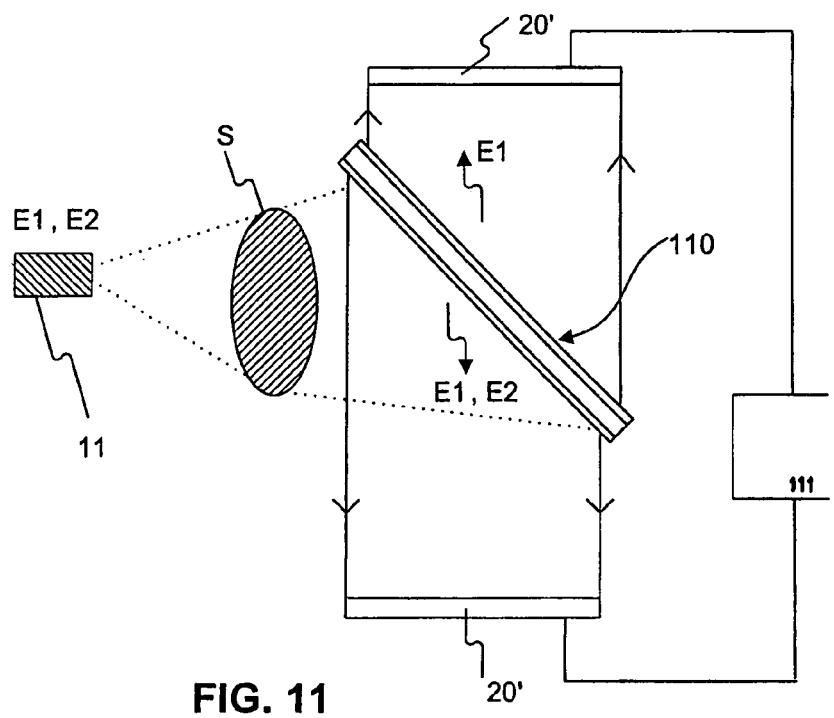
FIG. 11 is a schematic representation of another embodiment of the invention, where at least two different photosensitive sensors are associated to respective energy levels of the light.

Finally, another embodiment—which can be considered in itself or in combination with elements such as the pulse and gating described above—is illustrated in FIG. 11.

This figure shows a x-ray source 11 (pulsed or not) which illuminates a subject S, and an assembly 110 for receiving the x-rays after they passed through the subject.

The assembly 110 is a plate-shaped element which comprises a phosphor screen (or another type of converting means 12) on each of its faces.

Moreover, the central layer of assembly 110 is an energy filter which transmits only the rays having an energy higher than a given threshold—the rest of the x-rays being attenuated by this energy filter.

The source is operated at two different energies: E1 and E2 which is lower than energy E1.

This dual-energy operation can be carried out by successive pulses having respective energies E1 and E2, or by a simultaneous emission of rays having the two energy levels E1 and E2.

The energy filter of assembly 110 is defined so as to transmit (i.e. let through) only the x-rays with an energy at least equal to E1.

A first face of assembly 110 is directly exposed to the x-rays coming from the source and having passed through the subject.

The converting means arranged on this first face thus display a primary visible image which corresponds to both energies E1 and E2.

The second face of assembly 110 is not directly exposed to the x-rays. Only the x-rays which have been transmitted by the energy filter (the x-rays having an energy of E1 or more) impact the converting means on this face.

Thus, the converting means arranged on the two respective faces of assembly 110 do not exhibit the same primary image—even though these two primary images correspond to the same subject, at the same moment.

Each of these primary images is directed onto a respective module (20, or 20').

And the arrangement illustrated in this figure also comprises processing means 111 for retrieving the images from both modules, and combining them for any processing desired.

This arrangement can thus produce two images corresponding to two different energy levels, for the same subject at the same instant.

The processing means 111 can thus provide very efficient analysis on contrast, on the differential density within the subject (e.g. one image can address the tissues, and the other the bones . . . ), etc. . . .

The invention claimed is:

1. A radiology device, comprising:
an X-ray source for exposing a subject to radiation from said source;
means for converting the X-rays into optical images so as to form primary optical images;
a combination of n modules, n being an integer equal to or greater than two, each module forming a secondary optical image, each module having a module range of intensities expressed as the ratio between the maximum intensity which, can be detected and the minimum intensity which can be detected, each module having a gain from an image intensifier;
n−1 beam splitters, each beam splitter transmitting a transmitted beam of an intensity equal to a given ratio of an intensity of an incident beam and reflecting a reflected beam of an intensity equal to a remainder of the intensity of the incident beam;
each beam splitter being further arranged so that the beam respectively reflected by the beam splitter is directed onto a module associated to the beam splitter, and the beam respectively transmitted by the beam splitter is directed to another beam splitter or another module, the radiology device further comprising:
means for retrieving the n secondary images formed by the modules and for combining them on a time-coherent basis; and
means for displaying the secondary images to a user,
wherein each module is selectively and temporarily gated, each module being gated during a time window defining a specific gate conversion factor,
the radiology device further comprising synchronizing means, connected to the x-ray source and to each module, for synchronizing the gating of each module with an x-ray pulse from the x-ray source,
wherein each module comprises:
an optical chain, comprising in succession, from an output of the means for converting to an output of the module:
an assembly for optical intensification of the images; and
a photosensitive matrix sensor for forming said secondary images.

2. A radiology device according to claim 1, wherein a global range between a minimum and a maximum of intensity detectable by the combination of modules is wider than each module range.

3. A radiology device according to claim 1, wherein the synchronizing means are connected to at least one of the assembly for optical intensification and the photosensitive matrix sensor in each module.

4. A radiology device according to claim 1, wherein at least one module further comprises an image enlargement assembly in its optical chain.

5. The radiology device according to claim 4, wherein the image enlargement assembly is a variable enlargement assembly which enlarges the images according to a desired enlargement coefficient within a given range.

6. The radiology device according to claim 4, wherein the image enlargement assembly is made up solely of optical elements performing no discretization of the images.

7. The radiology device as claimed in claim 4, which comprises means for moving at least one element of the optical chain among a group consisting of the assembly for optical intensification of the images, the photosensitive matrix sensor and the image enlargement assembly, a movement being in a plane generally parallel to a midplane of the conversion means.

8. The radiology device according to claim 7, which comprises a central control unit for controlling the movement of the elements of the optical chain.

9. The radiology device according to claim 8, wherein the central control unit is physically distanced from other elements of the device.

10. The radiology device according to claim 1, which comprises means for monitoring the exposure and the degree of enlargement of the images.

11. The radiology device according to claim 1, wherein the assembly for optical intensification of the images comprises channel multiplier plate-type components.

12. The radiology device according to claim 1, which comprises means for digitizing the secondary images arising from the photosensitive matrix sensor.

13. The radiology device according to claim 12, which comprises interfaces for distributing the digitized secondary images destined for digital peripherals.

14. The radiology device according to claim 12, which comprises a screen for visualizing the digitized secondary images.

15. The radiology device according to claim 1, wherein the means for converting the X-rays into optical images consist of a fluoroscopy screen of the phosphor coating screen type.

16. The radiology device according to claim 1, wherein said optical chain is directed along a different axis from a normal to a midplane of the means for converting the X-rays into optical images, the radiology device further comprising:
    a mirror for deflecting the primary images to the optical chain; and
    a shield for protecting the optical chain from the X-rays.

17. The radiology device according to claim 1, wherein the optical chain comprises a refocusing lens.

18. The radiology device according to claim 1, which comprises a mirror for separating the images arising from the intensification assembly, and a digital video camera.

19. The radiology device according to claim 1, wherein the intensification assembly and the sensor are optically coupled by optical fibers.

20. A radiology process, comprising real-time medical examining a subject by means of a radiology device as claimed in claim 1.

21. A radiology process, comprising
    nondestructively qualitatively inspecting materials by means of a radiology device as claimed in claim 1, in particular in the industrial or maritime sector.

22. A radiology device according to claim 1, wherein each module is gated one time.

23. A radiology device according to claim 1, wherein each module is gated at two or more successive times following a single pulse of the x-ray source.

* * * * *